(12) United States Patent
Kirkjan

(10) Patent No.: US 12,228,557 B2
(45) Date of Patent: *Feb. 18, 2025

(54) MOISTURE DETECTION APPARATUS AND PROCESS

(71) Applicant: Desert Valley Date, Inc., Palm Desert, CA (US)

(72) Inventor: Gregory Paul Kirkjan, Palm Desert, CA (US)

(73) Assignee: Desert Valley Date, Inc., Coachella, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/656,834

(22) Filed: Mar. 28, 2022

(65) Prior Publication Data

US 2022/0373527 A1 Nov. 24, 2022

Related U.S. Application Data (63) Continuation of application No. 16/915,918, filed on Jun. 29, 2020, now Pat. No. 11,287,412, which is a continuation of application No. 16/100,997, filed on Aug. 10, 2018, now Pat. No. 10,697,949, which is a continuation of application No. 15/167,836, filed on May 27, 2016, now Pat. No. 10,048,241.

(60) Provisional application No. 62/256,646, filed on Nov. 17, 2015, provisional application No. 62/167,494, filed on May 28, 2015.

(51) Int. Cl.
*B07C 5/34* (2006.01)
*B07C 5/344* (2006.01)
*G01N 27/72* (2006.01)
*G01N 33/02* (2006.01)

(52) U.S. Cl.
CPC ........... *G01N 33/025* (2013.01); *B07C 5/344* (2013.01); *G01N 27/72* (2013.01); *B07C 2501/009* (2013.01)

(58) Field of Classification Search
CPC ..... B07C 5/34; B07C 5/344; B07C 2501/009; B07C 2501/0081; G01N 33/025; G01N 27/023; G01N 27/72
See application file for complete search history.

(56) References Cited

U.S. PATENT DOCUMENTS 2,228,901 A 1/1941 Wilcox
2,768,629 A 10/1956 Maul
(Continued)

FOREIGN PATENT DOCUMENTS

CN 208427408 U * 1/2019

*Primary Examiner* — Joseph C Rodriguez
(74) *Attorney, Agent, or Firm* — Knobbe, Martens, Olson & Bear, LLP (57) ABSTRACT

Embodiments of a water detection apparatus are disclosed that can detect characteristics of food products. The apparatus may include a conveying mechanism configured to move a food product through an aperture in the apparatus, a transmitter coil configured to transmit a signal within the aperture, and a receiver coil configured to receive the signal altered by the food product, and a signal processing unit configured to determine an output value associated with the food product moving through the aperture. The output value can be based, at least in part, on the signal and the altered signal. The output value can corresponds to a characteristic of the food product.

21 Claims, 7 Drawing Sheets

(56) References Cited

U.S. PATENT DOCUMENTS

| | | | |
|---|---|---|---|
| 3,966,973 | A | 6/1976 | Henry et al. |
| 4,045,657 | A | 8/1977 | Falke |
| 4,346,524 | A | 8/1982 | Wochnowski et al. |
| RE31,023 | E | 9/1982 | Hall, III |
| 4,547,725 | A * | 10/1985 | Oetiker ............ G01N 27/223 324/665 |
| 4,563,635 | A | 1/1986 | Wagner et al. |
| 5,671,633 | A | 9/1997 | Wagner |
| 6,020,744 | A | 2/2000 | Ghorashi et al. |
| 6,435,002 | B1 | 8/2002 | Briggs |
| 6,747,461 | B2 | 6/2004 | Corak et al. |
| 6,833,789 | B1 | 12/2004 | Carmen et al. |
| 7,265,351 | B2 | 9/2007 | Villers et al. |
| 7,591,374 | B2 | 9/2009 | Hunter et al. |
| 8,286,367 | B2 | 10/2012 | Kendall et al. |
| 8,860,443 | B1 | 10/2014 | Roberts |
| 9,201,056 | B2 | 12/2015 | Gordon et al. |
| 9,248,983 | B2 | 2/2016 | Streufert |
| 9,278,377 | B2 | 3/2016 | Brumback et al. |
| 9,442,055 | B2 | 9/2016 | Benedetti et al. |
| 9,486,839 | B2 | 11/2016 | Torek et al. |
| 10,048,241 | B2 | 8/2018 | Kirkjan |
| 10,697,949 | B2 | 6/2020 | Kirkjan |
| 11,287,412 | B2 | 3/2022 | Kirkjan |
| 2004/0211653 | A1 * | 10/2004 | Aisenbrey ............ H05K 3/101 428/323 |
| 2008/0191693 | A1 | 8/2008 | Jones et al. |
| 2012/0037545 | A1 | 2/2012 | Van Kasteren |
| 2012/0116572 | A1 | 5/2012 | Corak et al. |
| 2023/0210144 | A1 * | 7/2023 | Pujol ............ A23L 3/003 426/320 |

\* cited by examiner

MOISTURE DETECTION APPARATUS AND PROCESS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57 and made a part of this specification.

BACKGROUND

When some food products, such as fruit, are harvested, the food product is taken to a packing house with different levels of moisture content, for example, the fruit can be too wet, too dry, or just right for processing. The fruit can be sorted so that it can be properly prepared. For example, a fruit, such as a date, can be sorted into different moisture grades. It can be beneficial to sort fruit by moisture for both selling the fruit at the correct moisture level that meets customer specifications and for determining the amount of hydration or dehydration that the fruit requires during processing. After sorting, the fruit can be hydrated, kept in their current condition, or dried based on their grade so that the fruit will have substantially the same moisture and consistency.

SUMMARY OF EMBODIMENTS

The systems, methods, and devices of this disclosure each have several innovative aspects, no single one of which is solely responsible for the all of the desirable attributes disclosed herein.

In one embodiment, a water detection apparatus for detecting water content in a food product, the apparatus comprising: a conveying mechanism configured to move at least one food product through an aperture in the apparatus; at least one transmitter coil configured to transmit a signal within the aperture, wherein the at least one food product alters the signal; at least one receiver coil configured to receive the altered signal; and a signal processing unit configured to determine at least one output value associated with the at least one food product moving through the aperture based, at least in part, on the signal and the altered signal, wherein the at least one output value corresponds to water content of the at least one food product.

In another embodiment, a method for detecting characteristics of a food product, the method comprising: conveying at least one food product through an aperture in a detection apparatus; transmitting a signal, by at least one transmitter coil, within the aperture; receiving, by at least one receiver coil, a signal altered by the food product; determining at least one output value associated with the at least one food product moving through the aperture based, at least in part, on the signal and the altered signal, wherein the at least one output value corresponds to water content of the at least one food product, and processing the at least one food product based, at least in part, on the at least one output value.

In another embodiment, An apparatus for detecting characteristics in a food product, the apparatus comprising: a conveying mechanism configured to move at least one food product through an aperture in the apparatus; at least one transmitter coil configured to transmit a signal within the aperture, wherein the at least one food product alters the signal; at least one receiver coil configured to receive the altered signal; and a signal processing unit configured to determine at least one output value associated with the at least one food product moving through the aperture based, at least in part, on the signal and the altered signal, wherein the at least one output value corresponds to an metal detection characteristic and a water content characteristic of the at least one food product.

Although certain embodiments and examples are disclosed herein, inventive subject matter extends beyond the examples in the specifically disclosed embodiments to other alternative embodiments and/or uses, and to modifications and equivalents thereof.

BRIEF DESCRIPTION OF THE DRAWINGS

The foregoing aspects and many of the attendant advantages will become more readily appreciated as the same become better understood by reference to the following detailed description, when taken in conjunction with the accompanying drawings, wherein.

DETAILED DESCRIPTION

Fruit (e.g., dates) and/or other food product will sometimes require pre-hydration to soften the fruit and/or food product if it is too dry or dehydration to dry the fruit and/or food product if it is too wet. Moisture and water activity are measured to determine if a fruit needs to be hydrated or dried. Current methods involve sampling lots and measuring the moisture or water activity level (Aw) of the fruit and then steaming or drying the fruit in a room or chamber.

It can be very difficult to detect wet and dry fruits accurately. Infrared cameras and color cameras can be used to detect the moisture content of the fruit. The fruit can then be separated into wet and dry fruit. However, the current technology is not very accurate and the cameras can incorrectly categorize the fruit. In some instances, fruits may need to be wet in order for the camera to obtain a clear picture, which may add undesirable moisture to the fruit. Additional water in food products, such as dried fruits, can shorten the shelf life. For example, one problem with the current technology is that the visual outer appearance of dates can cause the cameras to incorrectly categorize the fruits.

Figure 1:
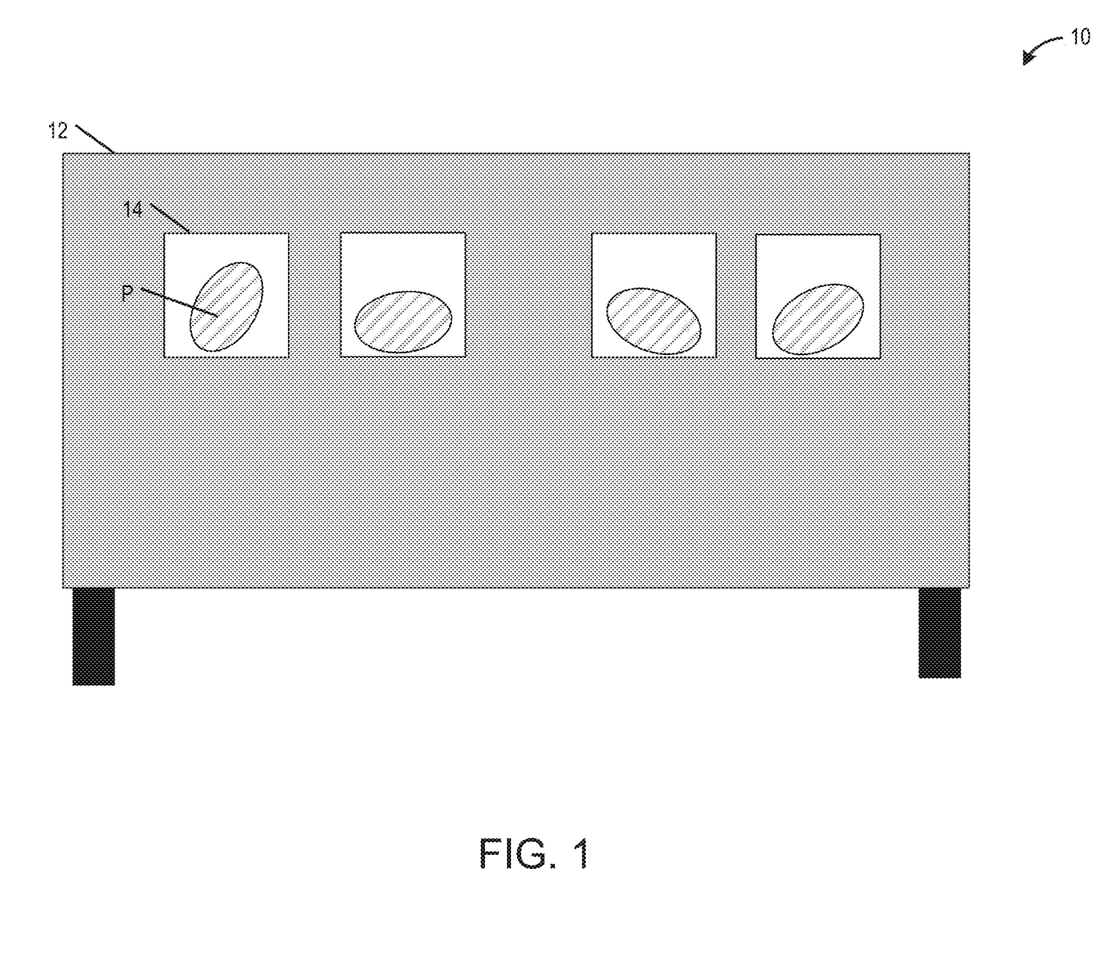
FIG. 1 illustrates an embodiment of a moisture detection apparatus.

FIG. 1 illustrates an embodiment of a water detection apparatus 10. The water detection apparatus 10 can have a housing 12 and a plurality of apertures 14. The food product P, such as a fruit, moves through each of the apertures. The product can be any type of food product, such as fruit, vegetable, a health or protein bar, or other food product for which a moisture level and/or water activity level of the food product is measured during processing. In one embodiment the product is a date. The product P can move through the apertures 14 on a conveying mechanism, such as a conveyor belt. The water detection apparatus 10 can operate using a coil loop detection system 20 (illustrated in FIG. 2). Each aperture 14 can have a separate coil loop detection system 20 dedicated to measuring the water activity level of the product moving through the aperture 14. The size of the aperture 14 can affect the accuracy of the measured water activity level (Aw). The size of the aperture 14 can be configured to fit the largest size of the fruit being measured without being too large. In some embodiments, decreasing the size of the aperture 14, such as the height and width, can increase the accuracy of the measured water activity level (Aw) for individual fruits. To further increase the accuracy one could presort the fruit by size such as height and then have different apertures for the different sizes to get a more accurate read on the individual fruits. In the illustrated embodiment, the water detection apparatus 10 has four apertures 14. In other embodiments, the apparatus 10 can be configured to have any number of apertures 14, such as, for example, two, three, eight, or any other number as required. In one embodiment, each aperture 14 can be two inches by two inches. Each aperture can have a separate set of coils that can be used to measure the product P moving through each aperture individually.

Figure 2A:
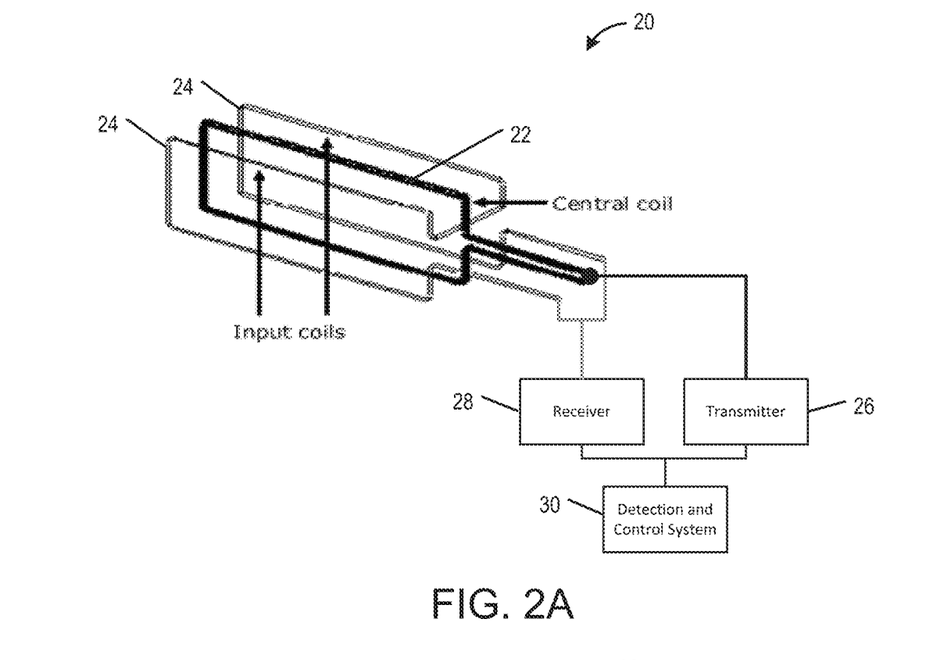
FIGS. 2A and 2B illustrate embodiments of coil loop detection systems.
Figure 2B:
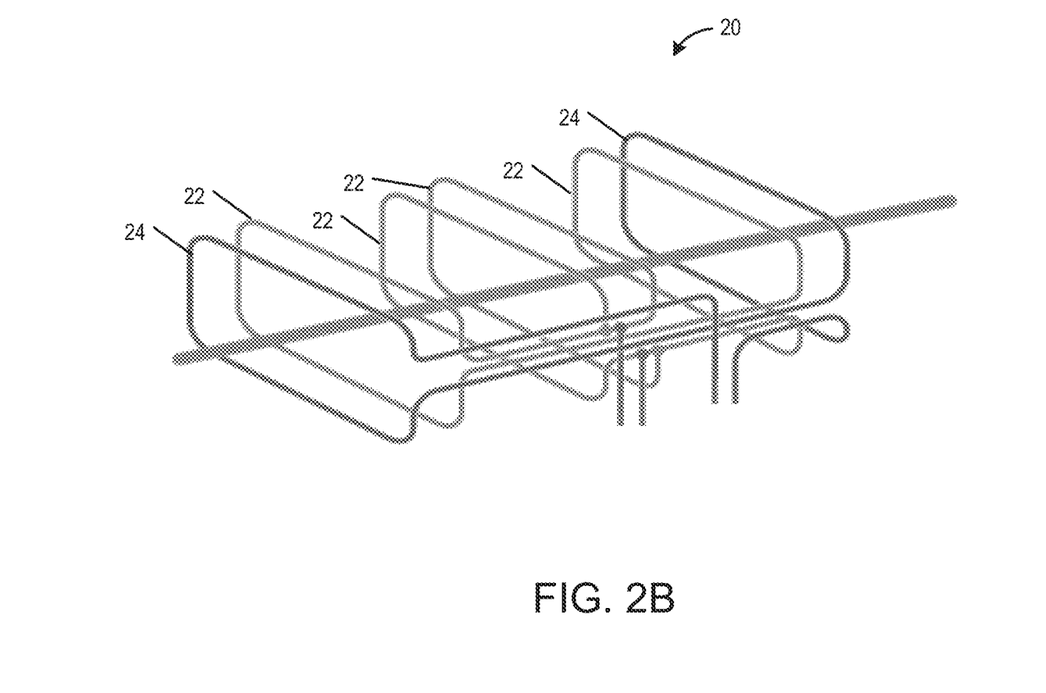

FIGS. 2A and 2B illustrate embodiments of the coil loop detection system 20. Each aperture 14 of the water detection apparatus 10 can include a coil loop detection system 20. The product P flows through the coils. The coil detection system can include at least one transmit coil 22, at least one receive coil 24, a transmitter 26, a receiver 28, and a detection and control system 30. The coils can surround the aperture 14. In the embodiment illustrated in FIG. 2A, the coil system 20 includes three equally spaced coils surrounding the aperture 14, two receive coils 24 on the outside and a transmit coil 22 in between. In some embodiments, such as in FIG. 2B, more than three coils can be used. In some embodiments, three pairs of coils, including a plurality transmit coils 22 and a receive coil 24 at each end. As illustrated, three pairs of oscillator coils can provide higher levels of sensitivity. In some embodiments multiple frequencies can provide higher sensitivity measurements. Parallel and series arrangements of coils can also be used. In some embodiments, the water detection apparatus 10 can use at least one coil to transmit a signal and at least one coil to receive the signal.

Generally, the coil loop detection system 20 uses at least one transmit coil 24 that connects to an oscillator circuit (e.g., a RF transmitter) 26 to produce a signal, which can create a magnetic field. The receive coils 22 on opposite ends of the transmit coil(s) 22 can receive the signal through the receiver 28 (e.g., an RF receiver). The receive coils 24 can be spaced apart from the transmit coils 22 such that they can receive equal amounts of signal. As one example, a receive coil 24 on either side of a single transmit coil 22 as illustrated in FIG. 2A. As another example, three sets of coils are illustrated in FIG. 2B. The transmit coils 22 and receive coils 24 can be wound in such a way that their signals oppose each other such that the net signal across them can be zero or substantially zero. When a product P enters the coils, the product P can disrupt the signal, such as the magnetic field (or field), around it. As the product passes through the field, it can change the balance of the receiving coils so that the net signal is no longer zero. A digital signal processor (DSP) in the detection and control system 30 can process the signal. The detection system 30 can perform product compensation, phasing, residual compensation filtering, and can categorize the fruit based on the received signal.

The detectors are capable of detecting changes in the product by measuring two effects: resistive and reactive effects. Electrically conductive materials and many food products by nature are electrically conductive. Salt and moisture content combine to produce resistive effects. Electrically conductive materials produce reactive effects. For example, iron is both electrically conductive and ferromagnetic. Dry products can produce very little or substantially zero product effect, whereas wet products can produce a larger product effect.

The measured magnetic field can change as a product moves through the field and the detection and control system 30 can derive reactive and resistive components associated with the product. When a product moves through the coils the ratio of resistive to reactive components is disrupted. For example, the detection system 30 can be used to measure the water activity level (Aw) in fruit by measuring the disruption in the magnetic field of the coils. By correlating numerical values with water activity level (Aw), the detection system 30 can measure the internal water activity level (Aw) of the fruit. The Product effect of the product P can disrupt the magnetic field similar to a metal object. The Product effect is based at least in part on the internal characteristics of the product that can disrupt the magnetic field of the Metal Detector. The Product effect is not limited to the ions of the product (e.g., the potassium contents of a date) or the bound or unbound water molecules. The size of the coils and the size of the aperture 14 that the product P moves through can affect the accuracy of the determination of a water activity level (Aw). To increase the accuracy the temperature of the product and/or environment can be regulated to obtain more accurate results. Product that is higher in temperature can also tend disrupt the magnetic field more than product that is at a lower temperature. Product that moves faster through the coils can disrupt the magnetic field more than a slower product.

Figure 4:
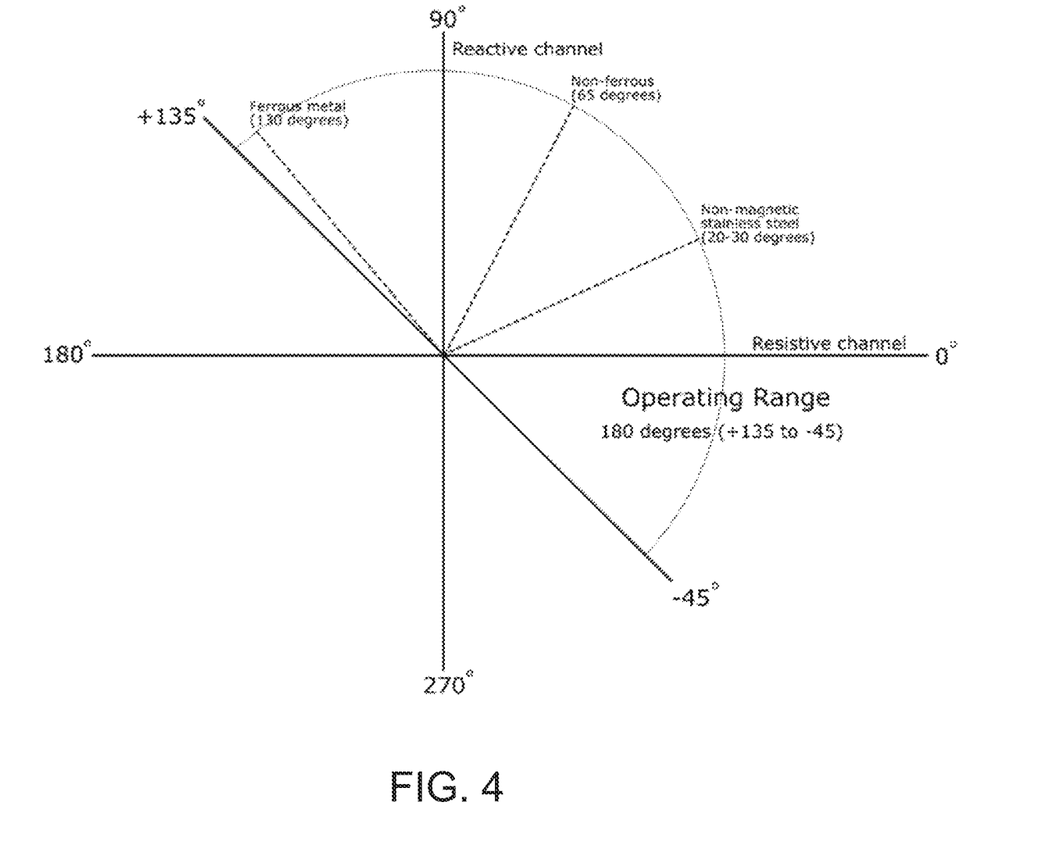
FIG. 4 illustrates an embodiment of a phase angle chart.

The detection system 30 can go through a learning phase, wherein the detection system 30 determines values associated with various water activity levels of a fruit product P. The system can measure the field changes and can derive reactive and resistive components. In one embodiment, the detection system 30 can convert the ratio between reactive and resistive components to a phase angle. FIG. 4 illustrates an embodiment of a phase angle chart illustrating an example of a phase angle based on the reactive and resistive components. In the illustrated embodiments, the approximate phase angle measurements correspond generally to +130 Metallic (ferrous) contaminants, such as iron; +90 Dry, non-conductive products, such as grains and cereals; +65 Non-ferrous metallic contaminants, such as copper; +20-30 Metallic contaminants, such as stainless steel; and 0 Wet, conductive products, such as fresh meats and breads.

Once this angle is determined, the detection system 30 can use this information to categorize the water activity level (Aw) of the fruit products P moving through the coils. For example, the detection system 30 can identify values associated with high and low water activity levels of dates. The learned values or ranges of values can be used to create thresholds associated with a fruit product P. Thresholds can be determined and maintained for resistive and reactive effects and can be used to detect different water activity levels (Aw).

Based on the extrapolated water activity level (Aw), the water detection apparatus can automatically sort the food product P. The sorting can use the determined thresholds or ranges of the water activity level (Aw). In some embodiments, the ranges can be programmed by the machine operator. Different ranges can be determined for each type of food product P.

Figure 3:
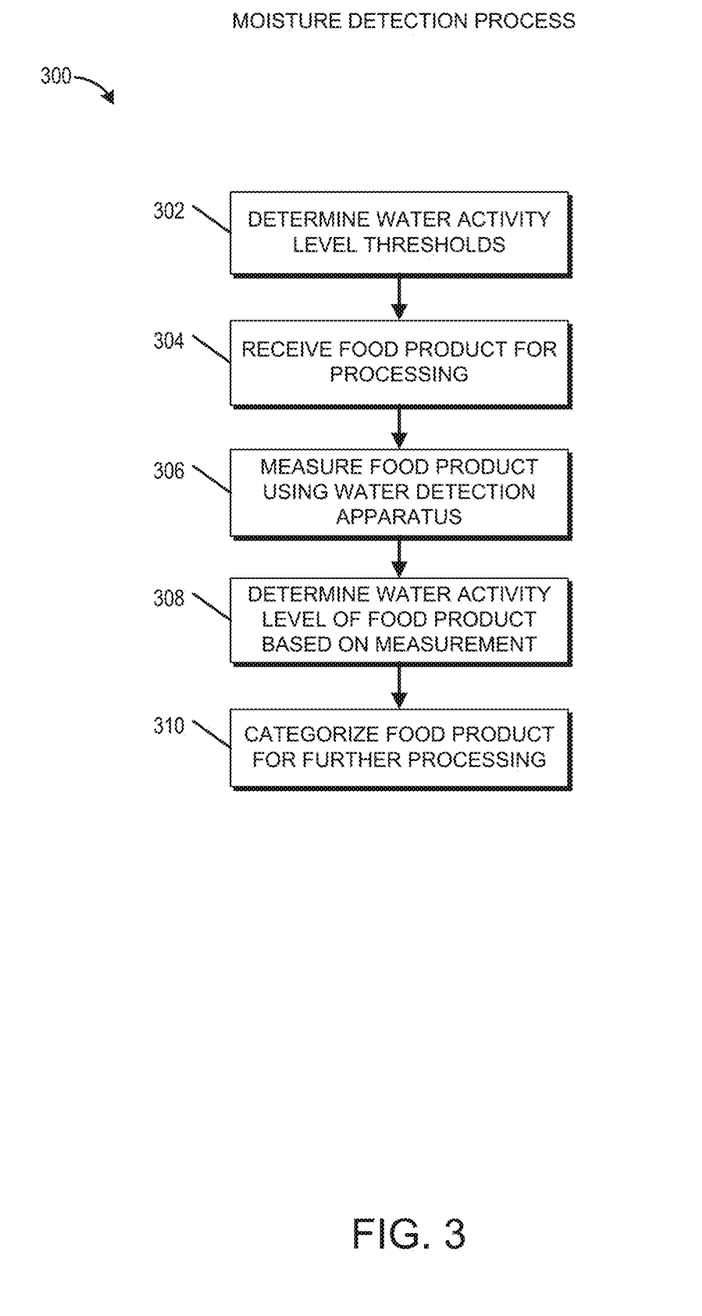
FIG. 3 illustrates an embodiment of a flow diagram of an illustrative process for determining water activity levels in food products.

FIG. 3 illustrates a process for measuring a water activity level in a food product that can be performed by water detection apparatus 10 discussed above. Though the process can be applied to many different types of fruits or other food products, the process will be described with respect to dates. At block 302, the water activity level thresholds for the dates are determined. The system can be used to identify a plurality of grades or groupings of the dates. In one embodiment, the dates can be grades that are wet, dry, and ready for processing. Each grade is associated with a numerical range for the determined water activity level (Aw). The ranges can be determined using empirical testing of the dates. This can also be referred to as the learning stage. After the learning stage is complete, the water detection apparatus can automatically associate the measurements of the fruit with one of the predetermined ranges.

At block 304, the dates are received for processing. At block 306, the dates are measured using the water detection apparatus. The dates are placed on a conveyer for sorting by the water detection apparatus 10. The dates can be positioned on the conveyer and moved through an aperture 14 of the water detection apparatus 10. In some embodiments, each date can be measured individually, in other embodiments the dates can measured on average in bulk. The dates may be positioned such that they are a determined distance apart in order to facilitate measuring the dates individually. The dates move through the aperture 14 and the coil loop detection system 20. The coil loop detection system 20 determines a measured value associated with the date.

In some embodiments, the food product (e.g., date) can be measured in bulk or measured quantities. For example, putting one pound of dates in a tub, the system can determine whether the plurality of food products have undesirable characteristics (e.g., dates that are either too wet or too dry). In some embodiments, consumer packs comprising a plurality of the food product can be measured and rejected as a single unit. Current methods rely on sampling which is not as accurate as measuring every item. Being able to measure Aw during a real time sorting operation can improve the quality and consistency of the packed consumer or bulk item.

At block 308, the system uses the measured value associated with the date to determine the water activity level (Aw) of the date based on the determined thresholds. At block 310, based on the determined water activity level (Aw), the dates are categorized for further processing using a reject system using pressurized air via nozzles timed to knock the product off a the conveyor belt onto another conveyor belt or bin/basket, or using a manual reject mechanism to throw the or push the date onto another convey belt or bin/basket. For example, dry dates can be categorized for further hydration and wet dates can be categorized for dehydration. In some embodiments, there can be a plurality of water activity levels and multiple sorts that further define the post-processing category. For example, different levels of hydration or dehydration may be required depending on the water activity level of the date.

Water Detection Apparatus

Figure 5:
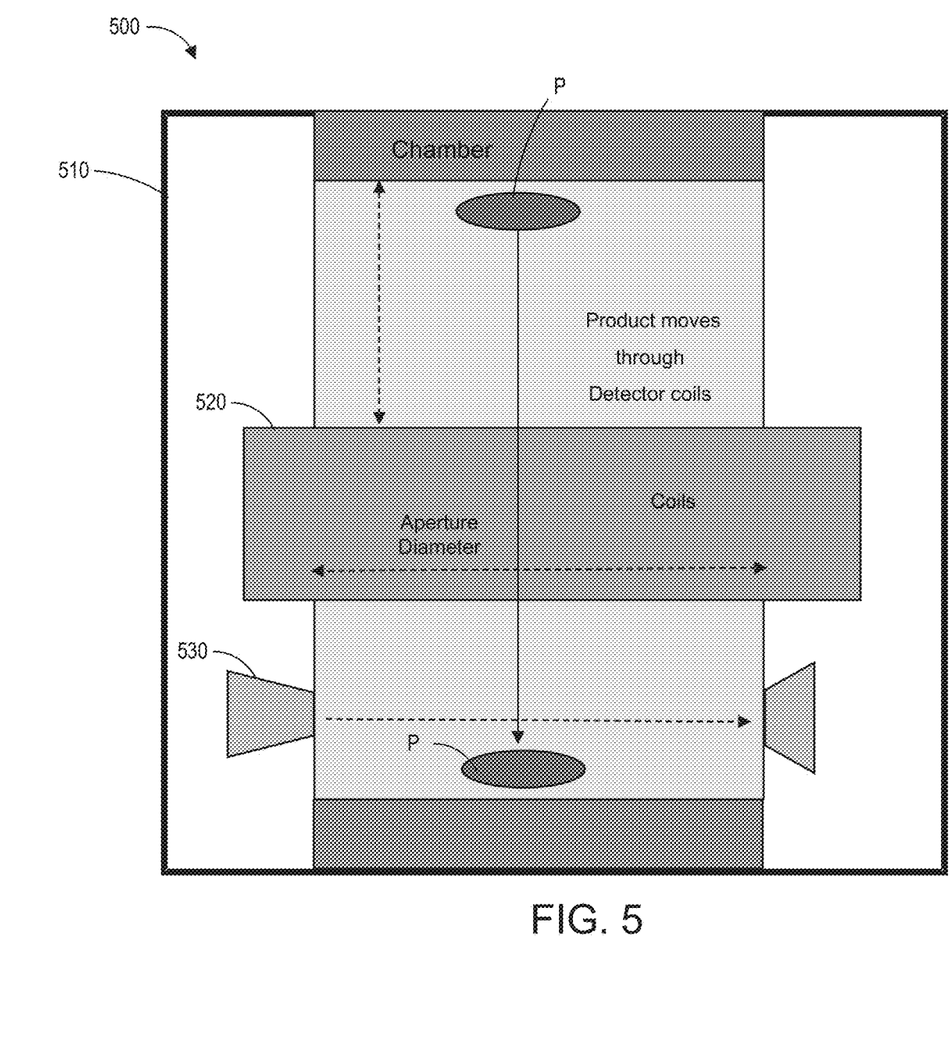
FIG. 5 illustrates an embodiment of a moisture detection test stand.

FIG. 5 illustrates an embodiment of a water detection apparatus 500. The water detection apparatus 500 can include a test cell housing 510, a coil detection system 520, and one or more optical detection systems 530. The test cell housing 510 can include a temperature sensor to determine the ambient temperature within the housing 510. The test cell housing can include a chamber that is configured to shield the test cell housing 510 and coil detection system 520 from electrostatic and electromagnetic interference. In some embodiments, the test cell housing includes a faraday shield or enclosure. In some embodiments, a distance between the chamber and the coil loop detection system 520 can be greater than the width of the aperture of the coil loop detection system 520, which can help to reduce interference between the chamber and the coil loop detection system 520.

In some embodiments, the water detection apparatus 500 can be configured to be vertically oriented. In a vertical orientation, the chamber can be positioned in the upper portion of the test cell housing 510. The chamber can be configured to release the food product. In some embodiments, the test cell housing 510 can have release mechanism, which can be mechanically and/or electrically actuated to drop the food product from the chamber of the housing 510. Gravity causes the food product to move from the chamber to the bottom of the housing 510. The food product can pass through an aperture in the coil loop detection system 620.

In some embodiments, the water detection apparatus 500 can be configured to be configured to be horizontally oriented. The food product can be configured to move through the aperture on a conveying mechanism, such as a conveyor belt. The speed at which the conveyor belt moves through the aperture can be controlled by an operator of the test chamber. In some embodiments, the speed of the conveyor is fixed at constant rate.

The water detection apparatus 500 can include one or more optical detection systems 530. In some embodiments, the optical detection system 530 can be configured to determine the speed of the food product at a defined point within the housing 510. In some embodiments, a plurality of optical speed detection systems can be used to determine the speed at a plurality of points during travel through the housing 510. In some embodiments, the optical detection system can include a temperature detection system. The temperature detection system can be used to determine the temperature of the food product. In some embodiments, the temperature detection system can be an infrared thermometer.

In some embodiments, the size of the food product can be determined by an optical detection system 530. The size of the food product may be based on various measurements, such as height, width, length, volume, mass, and/or other measurement parameters that can be used to determine a size of the food product. In some embodiments, the optical detection system 530 can include one or more optical measurement systems configured to determine measurements associated with the size and shape of the food product. The optical measurement systems may be configured to determine width, height, length, area, volume, and/or other measurements of the food product. In some embodiments, the optical measurement system can be configured to determine a length of the food product along two or more axes. In some embodiments, a weight sensor may be used to determine the mass or weight of the food product.

The coil loop detection system 520 can include at least one aperture (not shown). The food product P, such as a fruit, moves through the aperture. The product can be any type of food product, such as fruit, vegetable, or other product for which a water content or water activity level of the food product is measured. In one embodiment the product is a date. The product P can move through an aperture in order for the coil detection system to determine the water content or water activity level of the food product. The coil loop detection system 520 can operate as described above with respect to the coil loop detection system 20 (illustrated in FIG. 2). The size of the aperture can affect the accuracy of the measured water activity level. The size of the aperture can be configured to fit the largest size food product being measured without being too large. In some embodiments, decreasing the size of the aperture, such as the height and width, can increase the accuracy of the measured water activity level for individual food products. In some embodiments, the size of the aperture is based on the food product being tested. For example, a test system for determining a water activity level for dates can be smaller than a system for determining water activity level for avocados.

In some embodiments, the coil loop detection system 520 can be configured to determine the unbound or free water content value of the food product. In some embodiments, the unbound or free water content value of the food product can be directly related to a water detection sensitivity (WDS) value of the coil loop detection system 520. When the food product moved through the aperture, the coil loop detection system can determine a WDS value. In some embodiments, the WDS value can be a total value associated with the product effect of the food product by taking sample measurements of the food product as it moves through the coil. In some embodiments, the WDS can be an average value associated with the product effect of the food product. In some embodiments, the WDS value can be the peak product effect of the food product. The peak water content may provide a single value for a food product.

The detection and control system, such as the detection and control system 30 illustrated in FIG. 2A can be configured to determine the water activity level of the food product. In some embodiments, the control system can be configured to calculate a water content density by dividing the WDS value by a size of the food product. The size of the food product can be a linear value (for example, a length), an area (for example, a cross section of the food product), a volume, a mass/weight, or another measurement used for determining the size of the food product. The size of the food product can be determined automatically using one or more sensors, as described herein. In some embodiments, the size is an approximated size or average size of the food. By measuring and calculating a water content density, the accuracy of the determination of the water activity level of food product can be improved.

In some embodiments, compensation tables and/or algorithms can be implemented in firmware and/or software of the control system to determine the water activity level. In some embodiments, the determination of the water activity level can include a number of factors, such as, for example, the speed of the food product travelling through the aperture of the coil loop detection system 520, the temperature of the food product, and/or the size of the food product. Such algorithms can be used to determine the product effect by passing samples of the products of different Aw through the system, and system can determine how to correlate the Aw by measuring the product effect caused by the disruption of the field by the product.

The speed of food sample moving through the detector coils can alter the WDS value. In some embodiments, the WDS value increases with the speed of the food product. The temperature of the food product can affect the measurement. In some embodiments, the WDS value can have a direct correlation to the temperature of the food product. For example, the WDS value can decrease when the temperature of the food product decreases and increase when the temperature of the food product increases.

In some embodiments, a water activity level of the food product can be determined based, in part, on an analysis of the WDS value, the temperature, the speed, and the size of the food product. Each food product can have defined correlation tables that can be used to calculate the water activity level of the specific food product.

An advantage of this method is the speed at which a water activity measurement can be conducted. In the above described test system, the water content of the food product can be obtained within a shorter period of time. For example, the water detection apparatus can be configured to determine the water content level in less than 30 seconds, less than 20 seconds, less than 10 second, or less than 5 seconds. Using current methods, such as vapor pressure or an and optical sensor to measure water activity level can take up to 10 minutes as the testing apparatus has to wait for the vapor pressure to equalize. This can limit the number of samples that can be tested.

In some embodiments, the detector and control system can be configured to determine a ripeness index of a specific food product. For example, some thick-skinned fruits, such as, avocados, bananas, and citrus fruits, can include a ripening correlation table that can determine the ripeness index. As a fruit ripens, the WDS value can increase. In an illustrative example, the water content value of an avocado increases as it ripens because the avocado produces ethylene and water as a byproduct during ripening/decay. The water is prevented from escaping by the skin of the avocado, unlike more porous fruits, such as dates, which can allow moisture to evaporate.

Conveyor-Based Water Detection System

Figure 6:
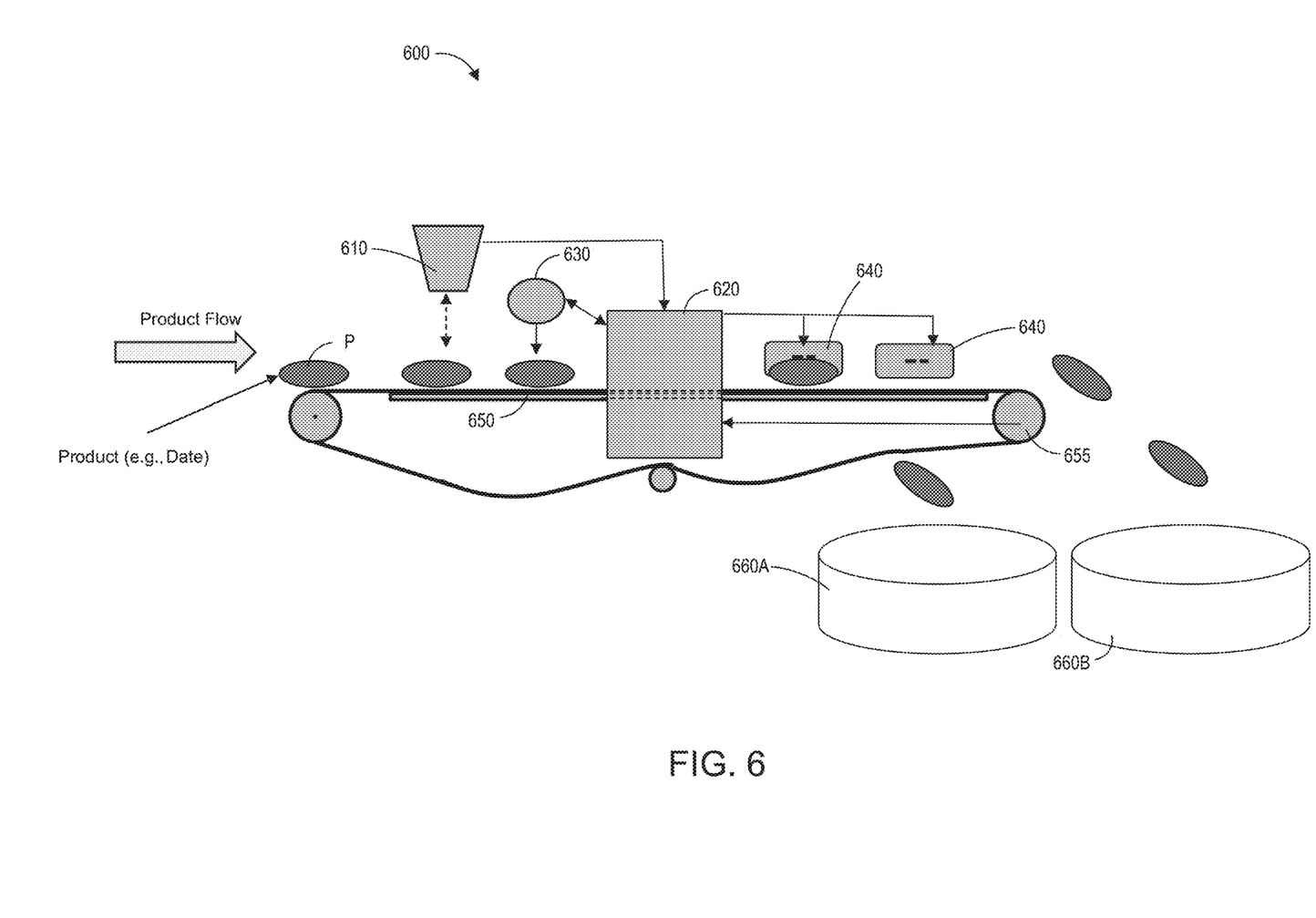
FIG. 6 illustrates an embodiment of a moisture detection system with a conveyor-based feed mechanism.

FIG. 6 illustrates an embodiment of conveyor-based water detection system 600. In this embodiment, the water detection system 600 includes a coil loop detection system 620. The coil loop detection system can have a plurality of apertures, such as illustrated in FIG. 1. The food product P, such as a fruit, moves through each of the apertures. The product can be any type of food product, such as fruit, vegetable, health bar or other product for which a moisture level or water activity level of the food product is measured during processing. In one embodiment the product is a date. The product P can move through the apertures on a conveying mechanism, such as a conveyor belt 650. The coil loop detection system 620 can operate as described above with respect to the coil loop detection system 20 (illustrated in FIG. 2). Each aperture can have a separate coil loop detection system dedicated to measuring the WDS value to obtain the water activity level of the product moving through the aperture. The size of the aperture can affect the accuracy of the measured WDS value to obtain the water activity level. The coil loop detection system can have any number of apertures. Each aperture can be referred to as a separate line. The food product can be indexed on each line such that the coil loop detection system can identify each food product individually. In some embodiments, the food product may be positioned within a holder on the conveyer belt, with each hold spaced apart at a defined distance. The speed of the conveyor 650 can be provided to the coil loop detection system used to measure WDS or another control system. In some embodiments, the speed of the conveyor can be determined by a shaft encoder 655 that can determine how fast the conveyor is moving the food product through the coil loop detection system 620.

The system 600 can include one or more temperature sensors 610, such as an IR thermometer. The temperature sensors can be configured to measure the temperature of individual food products (for example, dates). In some embodiments, there can be a temperature sensor for each line. In some embodiments, one temperature sensor can determine temperatures for multiple lines. The temperature information for each food product can be provided to the coil loop detection system 620.

An electronic measurement sensor 630, such as an optical sensor, can be configured to determine a measurement of the food product. For example, in one embodiment, the measurement sensor can determine the length of the food product. In some embodiments, a measurement sensor can be provided for each product line. In some embodiments, the measurement sensor 630 may also be configured to determine the speed of the food product moving along the conveyor. The size (for example, the length) of each food product can be provided to the coil loop detection system. In some embodiments, the measurement sensor can determine the position of the food product so the coil loop detection system 620 can determine when to sort the food product by blowing it off the conveyor.

The system 600 can include a plurality of pneumatic nozzles 640 configured to sort the food product into a plurality of sorting bins 660. The pneumatic nozzles 640 can be configured to knock the food product off the conveyor and into the sorting bins 660 using compressed air. In some embodiments, the pneumatic nozzles 660 can use compressed air at 60 to 90 psi. The coil loop detection system can provide instructions to the pneumatic nozzles in order to sort the food product. The illustrated embodiment includes sorting bins 660A and 660B, however, any number of sorting bins can be used. In some embodiments, the sorting bins 660 may also represent chutes or slides that transport the food product to another processing area or conveyor.

The coil loop detection system can be configured to determine the water activity level of each of the food product for use during sorting. The coil loop detection system can determine an estimated water activity level based, at least in part, on the food product temperature, the conveyor speed, the size of the food product, and the WDS value output by movement of the food product through the coils. In some embodiments, the coil loop detection system 620 can use additional or fewer factors to determine the water activity level. The water activity level can be compared to one or more threshold levels. The threshold levels can be used to categorize each of the food products for sorting. For example, a food product, such as dates, may be divided between wet, dry, and production ready dates. The dates can be categorized by the coil loop detection system 620 during runtime operation and automatically sorted into bins 660 by the pneumatic nozzles 640.

In another embodiment both Metal detection and Water activity and can be measured in one device. Generally, the product effect is outside the range used for metal detection and has as smaller peak signal than a piece of metal. The resistance-reactance ratio or phase angle at one or more frequencies and signal size can be used and interpreted by the system to distinguish between a metal object and the water content of a product. The system can be configured to have a plurality of rejection modes for a specific product, such as, for example, Wet, Dry, and metal rejection modes. The product having the desired characteristics can pass through without being rejected. The interpretation of the measured signal can be used to determine if the product includes undesirable characteristics such as metal, or being a wet or dry product. The measurement of the signal may be performed using various methods known in the art. In some embodiments it is desirable to have an Aw of less 0.70 to produce a shelf stable product.

Figure 7:
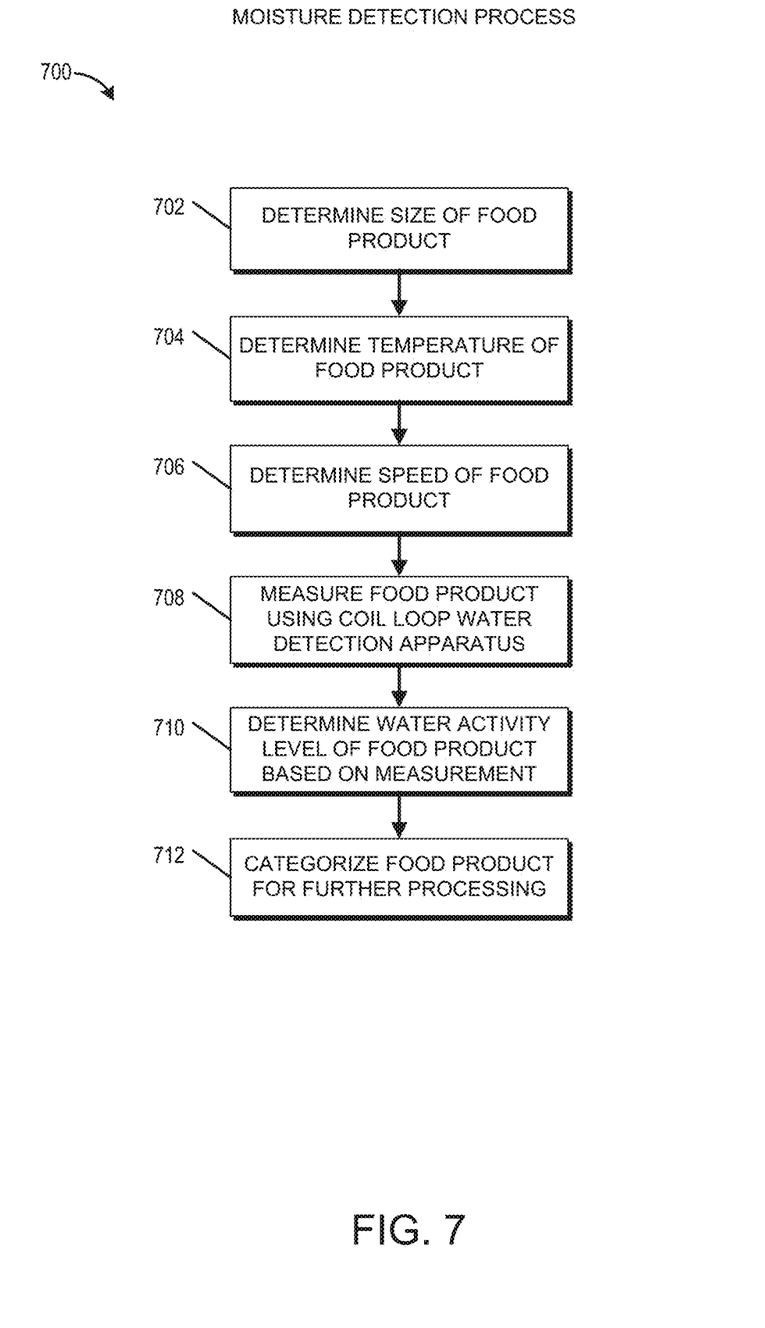
FIG. 7 illustrates an embodiment of a flow diagram of an illustrative process for determining water activity levels in food products.

FIG. 7 illustrates an embodiment of a flowchart of process for determining water activity in a food product. The process 700 can be implemented by a system configured to control the water activity detection system. For example, the process 700, in whole or in part, can be implemented by a detection and control system 30, or other computing system configured to control operation of aspects of the water activity detection system. Although any number of systems, in whole or in part, can implement the process 700, to simplify discussion, the process 700 will be described with respect to water activity detection systems.

At block 702, the system determines the size of the product. In some embodiments, the size of the food product can be determined by one or more sensors or a camera. The size of the food product may be based on various measurements, such as height, width, length, volume, mass, and/or other measurement parameters that can be used to determine a size of the food product.

At block 704, the system can determine the temperature of the food product. The temperature of the food product can affect the value of the measurement by the coil loop detection system. In some embodiments, the WDS value can have a direct correlation to the temperature of the food product. For example, the WDS value can decrease with when the temperature of the food product decreases and increase when the temperature of the food product increases.

At block 706, the system can determine the speed of the food product. The speed of food sample moving through the detector coils can alter the WDS value. In some embodiments, the WDS value increases with the speed of the food product.

At block 708, the dates are measured using the water detection apparatus. The food product is moved through an aperture of the water detection apparatus. The coil loop detection system determines a measured WDS value associated with each food product individually.

At block 710, the system uses the measured values associated with the food product to calculate and extrapolate the water activity level (Aw) of the food product. The coil loop detection system can determine an estimated water activity level based, at least in part, humidity of the atmosphere, on the food product temperature, the food product speed, the size of the food product, and the WDS value by movement of the food product through the coils. In some embodiments, the coil loop detection system 620 can use additional or fewer factors to determine the water activity level. The water activity level can be compared to one or more threshold levels to categorize the food product.

At block 712, based on the determined water activity level (Aw), the dates are categorized for further processing using a reject system using pressurized air via nozzles or mechanical movement timed to knock the product off a the conveyor belt onto another conveyor belt or bin/basket, or using a manual reject mechanism to throw the or push the date onto another convey belt or bin/basket. For example, dry dates can be categorized for further hydration and wet dates can be categorized for dehydration. In some embodiments, there can be a plurality of water activity levels and multiple sorts that further define the post-processing category. For example, different levels of hydration or dehydration may be required depending on the water activity level of the date.

Embodiments have been described in connection with the accompanying drawings. However, it should be understood that the foregoing embodiments have been described at a level of detail to allow one of ordinary skill in the art to make and use the devices, systems, etc. described herein. A wide variety of variation is possible. Components, elements, and/or steps may be altered, added, removed, or rearranged. Additionally, processing steps may be added, removed, or reordered. While certain embodiments have been explicitly described, other embodiments will also be apparent to those of ordinary skill in the art based on this disclosure.

Some aspects of the systems and methods described herein can advantageously be implemented using, for example, computer software, hardware, firmware, or any combination of software, hardware, and firmware. Software can comprise computer executable code for performing the functions described herein. In some embodiments, computer-executable code is executed by one or more general purpose computers. However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers.

While certain embodiments have been explicitly described, other embodiments will become apparent to those of ordinary skill in the art based on this disclosure. Therefore, the scope of the invention is intended to be defined by reference to the claims as ultimately published in one or more publications or issued in one or more patents and not simply with regard to the explicitly described embodiments.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A water detection apparatus for detecting water content in a food product, the apparatus comprising:
    a conveying mechanism configured to move at least one food product through an aperture in the apparatus;
    at least one transmitter coil configured to transmit a signal within the aperture, wherein the at least one food product alters the signal, wherein the at least one transmitter coil is positioned around the aperture such that the conveying mechanism is configured to move through the at least one transmitter coil;
    at least one receiver coil configured to receive the altered signal;
    a temperature sensor configured to detect a temperature of the at least one food product; and
    a signal processing unit configured to determine at least one output value associated with the at least one food product moving through the aperture based, at least in part, on the temperature, the signal, and the altered signal, wherein the at least one output value corresponds to water content of the at least one food product.

2. The apparatus of claim 1, where in the at least one output value of the water content is used to determine a water activity level of the at least one food product.

3. The apparatus of claim 2, wherein the at least one output value is a numerical value corresponding to the water activity level and is associated with a predetermined range of numerical values.

4. The apparatus of claim 3, wherein the range of numerical values is predetermined.

5. The apparatus of claim 1, wherein the apparatus is configured to post-process the at least one food product based on the at least one output value.

6. The apparatus of claim 5, wherein the post-process associated with the at least one output value is hydrating, dehydrating, or doing nothing to the at least one food product.

7. The apparatus of claim 1, wherein the at least one food product is a fruit.

8. The apparatus of claim 7, wherein the signal processing unit is further configured to determine a ripeness index associated with the fruit.

9. The apparatus of claim 1, wherein the at least one food product is a date.

10. The apparatus of claim 1, wherein the at least one food product comprises a plurality of food products, and wherein the apparatus is configured to determine the at least one output value associated with the plurality of food products as an individual food product.

11. The apparatus of claim 1, wherein a height and width of the aperture are sized to be within a defined distance of the food product.

12. The apparatus of claim 1, wherein the temperature of at least one of the food product or environment is maintained within a defined temperature range.

13. The apparatus of claim 2, wherein the determination of the water activity level is based, at least in part, on at least one of humidity, speed, size, or temperature of the food product.

14. The apparatus of claim 13, wherein signal processing unit is configured to use the water activity level based on a correlation between the at least one output value and at least one of humidity, speed, size, or temperature of the food product.

15. The apparatus of claim 13, wherein the size includes at least one of length, area, volume, mass, or weight of the food product.

16. A method for detecting characteristics of a food product, the method comprising:
    conveying at least one food product through an aperture in a detection apparatus;
    detecting, by a temperature sensor, a temperature of the at least one food product;
    transmitting a signal, by at least one transmitter coil, within the aperture, wherein the at least one transmitter coil is positioned around the aperture such that the at least one food product moves through the at least one transmitter coil;
    receiving, by at least one receiver coil, a signal altered by the food product;
    determining at least one output value associated with the at least one food product moving through the aperture based, at least in part, on the temperature, the signal, and the altered signal, wherein the at least one output value corresponds to water content of the at least one food product, and
    processing the at least one food product based, at least in part, on the at least one output value.

17. The method of claim 16, wherein processing the at least one food product comprises rejecting the at least one food product if the at least one output value is within a defined range of output values.

18. The method of claim 16 further comprising determining at least one metal detection output value associated with the at least one food product moving through the aperture based, at least in part, on the signal and the altered signal, wherein the at least one metal detection output value corresponds to a metal detection indication of the at least one food product.

19. The method of claim 16, wherein the at least one food product comprises a plurality of food products, and wherein the at least one output value corresponds to the plurality of food products.

20. An apparatus for detecting characteristics in a food product, the apparatus comprising:
    a conveying mechanism configured to move at least one food product through an aperture in the apparatus;
    at least one transmitter coil configured to transmit a signal within the aperture, wherein the at least one food product alters the signal;
    at least one receiver coil configured to receive the altered signal; and
    a temperature sensor configured to detect a temperature of the at least one food product;
    a signal processing unit configured to determine at least one output value associated with the at least one food product moving through the aperture based, at least in part, on the temperature, the signal, the signal and the altered signal, wherein the at least one output value corresponds to a metal detection characteristic and a water content characteristic of the at least one food product.

21. The apparatus of claim 20, wherein the apparatus is further configured to determine whether to reject the at least one food product based, at least in part, on at least one of a comparison of the metal detection characteristic to a metal detection criteria or a comparison of the water content characteristic to water content rejection criteria, wherein the metal detection rejection criteria is different that the water content rejection criteria.

* * * * *